United States Patent
Kowal et al.

(10) Patent No.: US 9,277,861 B2
(45) Date of Patent: Mar. 8, 2016

(54) AUTOMATIC IMAGE OPTIMIZATION SYSTEM, PARTICULARLY FOR STEREOMICROSCOPES

(71) Applicant: UNIVERSITÄT BERN, Bern (CH)

(72) Inventors: Jens Kowal, Seftigen (CH); Tobias Rudolph, Bern (CH); Christoph A. Amstutz, Bern (CH)

(73) Assignee: UNIVERSITÄT BERN, Bern (SE)

( * ) Notice: Subject to any disclaimer, the term of this patent is extended or adjusted under 35 U.S.C. 154(b) by 85 days.

(21) Appl. No.: 14/365,234

(22) PCT Filed: Dec. 14, 2012

(86) PCT No.: PCT/EP2012/075612
§ 371 (c)(1),
(2) Date: Jun. 13, 2014

(87) PCT Pub. No.: WO2013/087872
PCT Pub. Date: Jun. 20, 2013

(65) Prior Publication Data
US 2015/0002816 A1    Jan. 1, 2015

(30) Foreign Application Priority Data

Dec. 14, 2011 (EP) .................................... 11193583

(51) Int. Cl.
| A61B 3/14 | (2006.01) |
| A61B 3/00 | (2006.01) |
| A61B 3/15 | (2006.01) |
| G02B 21/22 | (2006.01) |
| A61B 3/117 | (2006.01) |

(52) U.S. Cl.
CPC ................. *A61B 3/156* (2013.01); *A61B 3/117* (2013.01); *G02B 21/22* (2013.01)

(58) Field of Classification Search
USPC .................................. 351/206, 207, 208, 246
See application file for complete search history.

(56) References Cited

U.S. PATENT DOCUMENTS

| 4,452,517 A | 6/1984 | Kohayakawa |
| 2008/0204660 A1 | 8/2008 | Obrebski |

FOREIGN PATENT DOCUMENTS

| DE | 30 01 244 A1 | 7/1980 |
| DE | 10 2006 038911 A1 | 2/2008 |
| EP | 1 891 890 A1 | 2/2008 |
| EP | 2 248 460 A1 | 11/2010 |
| WO | WO 2010/129775 A1 | 11/2010 |

OTHER PUBLICATIONS

Ledfrod et al., "The Slit Lamp Primer", 2nd Edition, pp. 1-9, 2006.
Pavel Holoborodko "Noise Robust Gradient Operators", Jul. 27, 2009 obtained from http://www.holoborodko.com/pavel/image-processing/edge-detection.

*Primary Examiner* — Jack Dinh
(74) *Attorney, Agent, or Firm* — Birch, Stewart, Kolasch & Birch, LLP

(57) ABSTRACT

The invention relates to a device for examining an eye, particularly a human eye, comprising: an optical unit that is designed to generate a current image of a current intermediate image, wherein the optical unit comprises an objective, an additional lens that is designed to be arranged in front of an eye along an optical axis of the optical unit in order to generate said current intermediate image of a posterior structure of said eye, and wherein said additional lens is designed to be movable relative to said optical unit so as to generate a sharp and particularly reflection-free current image of said posterior structure with help of said optical unit. According to the invention, the device comprises a first actuator means that is designed to move the additional lens and which is controlled depending on the current image. Furthermore, the invention relates to a method for examining an eye.

57 Claims, 5 Drawing Sheets

AUTOMATIC IMAGE OPTIMIZATION SYSTEM, PARTICULARLY FOR STEREOMICROSCOPES

The invention relates to a device for examining an eye, particularly a human eye according to the preamble of claim 1 as well as a method for examining an (e.g. human) eye.

Such a device usually comprises an optical unit having at least one objective, wherein said optical unit particularly comprises a stereomicroscope (or is formed as a stereomicroscope). Particularly, a stereomicroscope is an optical microscope variant being designed for observing a sample using incident light illumination rather than transillumination. It uses two separate optical paths having each an objective and an eyepiece (ocular) to provide slightly different viewing angles to the left and right eyes of the observer using the microscope. In this way it produces a three-dimensional visualization of the sample being examined. A detailed description of such a stereomicroscope is given in Ledford, Janice K. and Sanders, Valerie N. "The slit lamp primer", 2nd Edition, SLACK Incorporated, ISBN 13 978-1-55642-747-3, published 2006.

The optical unit is designed to generate a current image (that can be seen by an ophthalmologist, e.g. through at least one ocular of said optical unit) of a current intermediate image, an additional lens (e.g. convex lens) that is designed to generate said intermediate image of a posterior structure (e.g. retina) of an eye that is to be examined, wherein said additional lens is arranged in front of said objective along an optical axis of said optical unit, and wherein said additional lens is designed to be arranged in front of said eye along the optical axis in order to generate said intermediate image. Further, said additional lens is designed to be movable by means of a first actuator means with respect to said optical unit so as to particularly increase sharpness of the current image and to reduce reflections of the current image of said posterior structure (retina) observed with help of said optical unit.

Such optical units, particularly stereomicroscopes employing lighting units in form of slit-lamps, are very often used in the ophthalmic field because they offer stereoscopic visualization of the anatomical structures and provide an unmatched flexibility compared to other devices in observing both posterior and anterior structures of an eye.

In particular, imaging the posterior part of the human eye using a slit lamp is a very common investigation to assess pathologies of posterior structures like the retina, the optic nerve head, and other posterior structures of the eye.

For intraocular observations the ophthalmologist uses an additional lens, which has to be manually aligned in the optic path (i.e. along the optical axis) between the objective and the eye of the patient in order to create a sharp image from the posterior structure. The challenge however is to bring the complete optical system consisting of the operator's (doctor's) eye, the optical unit (slit lamp), the additional lens, and the patient's eye into an alignment to guaranty an optimal image quality. Moreover, an optical unit employing a lighting unit such as a slit lamp images just a rather small portion of the posterior structure (e.g. retina) at a time, so that the ophthalmologist has to scan said structure (retina) in horizontal and vertical directions to get a complete overview. While doing this, he has to continuously improve the overall alignment to get a sharp current image of the structure to be examined with as few as possible reflections. Most of such reflections are caused by the additional slit-like illumination of an employed lighting unit (e.g. slit lamp) passing the additional lens to illuminate the fundus.

Several attempts have been made in the past to reduce the reflections and glare in ophthalmic imaging devices. In EP 2 248 460 one seeks to determine an optimal position for the additional lens for a specific lens system and a specific light incident angle, which should result in an optimal image. The additional lens is translated into a position that is optimal according to the theoretical model for that lens.

Other attempts e.g. such as DE 10 2006 038 911 or WO2010/129775 suggest to bypass the illumination around the additional lens and to couple the light into the system behind the additional lens.

In EP 1 891 890 optical damping elements are proposed in order to reduce glare and reflections.

In general, it can be stated that for each alignment of the (ophthalmic) device and the lighting unit (light source) in relation to the patient's fundus an optimal lens position exists that creates a sharp image and that exposes a minimal amount of reflections in the current image.

Based on the above, the problem underlying the invention at hand is to provide for a device and a method that allows for a simplification of the above-mentioned posterior structure observations.

This problem is solved by a device having the features of claim 1.

According thereto, the device comprises a first actuator means being designed to be controlled by the device depending on the current image, particularly in real-time, particularly by means of a closed feedback (control) loop (so as to generate a sharp and particularly reflection-free/glare-free current image of the respective posterior structure).

Moving the additional lens may thereby correspond to a translation of the lens along/across the optical axis (optical path) thus changing the spatial position of the additional lens as well as to changing the orientation of the additional lens in space (i.e. tilting the lens). Thus, in the following, position has the components spatial position and orientation. Each of which may also be changed alone.

Particularly, the optical unit comprises at least one camera for capturing said current image, wherein said at least one camera is particularly formed by a CCD camera. In case the optical unit comprises a stereomicroscope or is formed as such a microscope also two such cameras may be employed in order to capture both view channels of said microscope.

Thus, the at least one camera is designed to generate a series of (current) images of the respective posterior structure to be examined (e.g. retina), i.e., a live-stream. As long as all components of the system (as well as the patient's eye) are static, the current image is also static (not changing with time).

In order to control the first actuator means, the device according to the invention particularly comprises a first controlling unit of the actuator means.

Further, the device particularly comprises an analyzing unit being designed to analyze (process) the respective current image in order to determine at least one or a plurality of parameters being associated to the current image. Such a parameter may be the ratio between the size of a (connected) region (sub-image) of the current image containing information about the observed posterior structure (e.g. retina information) and the size of a reflection region of said image (first parameter). In this regard, a region may be a connected region or also a plurality of separate (adjacent) regions.

Furthermore, also the sharpness of said region of the image containing posterior structure information may be determined as a second parameter.

According to an aspect of the invention, the analyzing unit is designed to determine (depending on the first and second parameter, for instance) a position into which the additional lens is to be moved and to maximize said at least one parameter (e.g. said ratio and/or said sharpness) with respect to the position of the additional lens (spatial position for increasing sharpness and orientation for reducing reflections/glare, i.e. increasing said ratio).

In this regard, the first controlling unit is particularly designed to control the first actuator means for moving the additional lens into the respective new position (i.e. new spatial position and/or new orientation) of the additional lens determined by the analyzing unit, thus generating a new current image.

Thus, particularly, the at least one camera generating (or capturing) a current image of the posterior structure of the observed eye, the analyzing unit and the first controlling unit of said first actuator means form a closed feedback control loop, wherein the current image is analyzed by means of the analyzing unit in order to determine said parameters, then the additional lens is moved—with help of the first controlling unit controlling the first actuator means—into a new position (new spatial position and/or new orientation) determined by the analyzing unit leading to a new current image which is again analyzed by the analyzing unit in order to determine said parameters again, wherein the additional lens is moved such that said parameters are maximized (optimized). Particularly, the analyzing unit is designed to determine a new position of the additional lens depending on said parameters by means of a known Simplex algorithm, wherein particularly said closed feedback control loop is designed to maximize said two parameters (ratio and sharpness) separately, since said ratio predominantly depends on the orientation (tilting) of the additional lens whereas said sharpness predominantly depends on the spatial position of the additional lens along the optical axis of the optical unit.

Thus, the system (device) according to the invention does not restrict in any way the investigation of the ophthalmologist, but frees the latter during the investigation from the challenging task of manually holding and aligning the additional lens in the optical system between the patient's eye and the optical unit.

Furthermore, the proposed invention assesses the content of the current image as seen by the ophthalmologist and adjusts the position and orientation of the additional lens so as to improve the quality of the image.

In this regard, the invention at hand does not make any assumptions about the optical properties of the complete optical system, but derives the current image of the respective posterior (or other eye) structure seen by the ophthalmologist and analyses it in real-time. It can therefore be easily adapted to various types of optical units, particularly stereomicroscopes.

Based on the above-described real time analysis of the current images the ophthalmologist sees during the investigation, the device according to the invention will iteratively optimize the spatial position and orientation of the additional lens by means of said (mechanical) actuator means. It may therefore be considered as an advanced autofocus system, which does not only adjust the focus to get a sharp image but also the spatial position and orientation of the additional lens in order to reduce glare and reflection in the current image captured by the at least one camera.

As mentioned before, the first actuator means is particularly designed to adjust the spatial position and/or orientation of the additional lens with respect to the optical unit (in general moving the additional lens along the optical axis, i.e., altering the spatial position, changes the sharpness of the current image seen by the ophthalmologist, whereas tilting the lens (i.e. changing its orientation) reduces glare and reflections).

Particularly, the first actuator means is formed as a parallel kinematics and comprises a first, a second and a third linear actuator (e.g. electrical linear motor), wherein each of the linear actuators comprises a first element and a second element, wherein the second element is guided by its respective first element and can be moved with respect to the respective first element along an extension direction of the respective second element. Particularly, the second elements are each connected with a free end via two revolving joints to a first retainer retaining the additional lens, wherein the first elements are each connected to a second retainer via a revolving joint, which second retainer is particularly rigidly connected to the optical unit and opposes the first retainer along the optical axis. Particularly, said revolving joints are arranged such that the additional lens can be translated along the optical axis back and forth and also tilted about two linearly independent axes.

In order to illuminate the fundus (posterior structure), the device according to the invention particularly comprises a lighting unit (light source), particularly in the form of a slit lamp that is designed to generate a light beam along the optical axis of the optical unit (i.e. along the optical path), wherein the lighting unit particularly comprises a mirror for reflecting the light beam along the optical axis (i.e. for coupling said light beam into the at least one optical path of the optical unit).

In this context, the lighting unit is particularly configured such that it can be rotated about a vertical axis (related to a state of the device in which the latter is positioned as intended, i.e. in an operable state) in order to adjust an incidence angle with which said light beam impinges on the additional lens (i.e. the angle between the light beam and an extension plane along which the additional lens extends).

In order to also optimize said incidence angle, the device according to the invention particularly comprises a second actuator means for rotating (pivoting) the lighting unit about the vertical axis. Thereby, the device according to the invention comprises a second controlling unit being configured to control the second actuator means for rotating/pivoting the lighting unit.

In a variant of the invention, the analyzing unit is now also designed to determine, depending on the first parameter, a new incidence angle of the light beam and to maximize the first parameter with respect to the position of the additional lens (spatial position and orientation) and the incidence angle of the light beam.

In this regard, the second controlling unit is particularly designed to control the second actuator means for rotating the lighting unit so that the light beam hits/approaches the additional lens with the new incidence angle as determined by the analyzing unit.

Thus, particularly, the at least one camera generating (or capturing) a current image of the retina, the analyzing unit and the controlling units of said actuator means form a closed feedback control loop, wherein the current image is analyzed by means of the analyzing unit in order to determine said parameters, then the additional lens is moved and the incidence angle is changed—with help of the respective controlling units controlling the respective actuator means—as determined by the analyzing unit leading to a new current image which is again analyzed by the analyzing unit in order to determine said parameters again, wherein the additional lens is moved and the incidence angle is adjusted such that said parameters are maximized (optimized), particularly, the analyzing unit is designed to determine a new position of the additional lens depending on said parameters by means of a known Simplex-algorithm, wherein particularly said closed feedback control loop is designed to maximize said two parameters (ratio and sharpness) separately, see above.

In a variant of the Invention, the optical unit comprises a stereomicroscope (or is formed as such a microscope) having said objective as well as at least one ocular through which the ophthalmologist can perceive the current image of the observed structure.

Further, the device according to the invention particularly comprises a carrier for supporting the optical unit, which carrier is configured to be movable along a horizontal direction (for instance towards and away from a patient whose eye is to be examined), wherein particularly the device comprises a third actuator means that is configured to move the carrier along said horizontal direction.

Particularly, the optical unit is connected to said carrier via a revolving joint so that the optical unit can be rotated about a vertical axis, wherein particularly the device comprises a fourth actuator means that is designed to rotate the optical unit about said vertical axis. Further, the optical unit is preferably connected to the carrier such that it can be adjusted (displaced) along a vertical direction with respect to the carrier, wherein particularly the device according to the invention comprises a fifth actuator means that is configured to move the optical unit along said vertical direction.

Particularly, said lighting unit (slit-lamp) is also connected to the carrier via a revolving joint such that it can be rotated (pivoted) about a vertical axis, which may be the same vertical axis about which the optical device can be rotated/pivoted.

In order to trigger said actuator means described above and initiate the stated adjustments, the device according to the invention preferably comprises a manually operable actuating means, for instance in the form of a joystick.

Furthermore, the problem underlying the present invention is also solved by a method for examining an (e.g. human) eye, particularly using a device according to the invention, wherein said method comprises the steps of: Arranging an additional lens between the eye to be examined and an objective of an optical unit so as to generate a current image of a posterior structure of the eye (or any other structure of the eye) by means of said optical unit and said additional lens, and moving said additional lens automatically with respect to said objective depending on the current image (particularly in real-time by means of a feedback control, see above) in order to reduce reflections and/or increase the sharpness of said current image.

Particularly, the current image is captured by at least one camera, particularly a CCD camera, so that the current image is particularly represented by a plurality of pixels.

In a variant of the method according to the invention, at least one parameter associated to the current image is automatically determined, wherein particularly the ratio between the size of a (connected) region (sub-image) of the current image containing posterior structure information (or other eye structure information) and the size of a reflection region of said image (e.g. a reflection/glare spot) is determined as a first parameter. Further, also the sharpness of said region of the current image containing said structure information is determined as a second parameter.

In order to compute (estimate) said first parameter, each pixel of the current image is particularly automatically classified to belong to either background containing no (posterior) structure information, said region containing said structure information, or said reflection region (e.g. glare spots), wherein said classification is preferably performed using a Bayesian classifier. The regions may be connected, but may also consist of a plurality of separate regions, see above. Further, in this respect, a Bayesian network also known as belief network can be used to implement such a classifier. Based on a training set of (slit lamp) images, the probability that a pixel in the image belongs to either background, content (said (posterior) structure information), or reflection can be determined using pixel properties such as pixel color information, entropy in the local pixel environment, or pixel position.

In order to compute (estimate) said second parameter, said region containing (posterior) structure information is filtered by performing a first partial differentiation of its intensity (e.g. an approximated first partial derivative operator may be applied to the intensity of said region, which may also incorporate a smoothing function), wherein such a gradient operator may comprise a Holoborodko Kernel (i.e. a convolution of said intensity with said kernel is automatically performed) as disclosed in Pavel Holoborodko, Noise Robust Gradient Operators, http://www.holoborodko.com/pavel/image-processing/edge-detection/, 2009], and the pixel distribution of the outcome is computed (particularly by automatically computing a histogram giving the number of pixels that have the same intensity (which intensity is proportional to the amount of light reflected by the corresponding point on the object in the direction of the viewer), wherein in case said pixel distribution within the histogram is rather equal, the region containing (posterior) structure information (sub image) is rather blurry. The more significant the peaks are in said histogram of said sub image, the sharper said sub image is (for instance two sharp peaks).

Particularly, these two parameters are now automatically maximized (optimized) with respect to the position of the additional lens, particularly with respect to the spatial position of the additional lens along the optical axis (path) as well as the orientation (tilting) of the additional lens. In this respect, the first parameter may be additionally also maximized with respect to an incidence angle of a light beam generated by a lighting unit (e.g. slit lamp) for illuminating the (posterior) structure to be examined, with which incidence angle said light beam impinges on the additional lens.

Particularly, the first and second parameters are maximized (optimized) separately, see above, because the sharpness depends on the spatial lens position along the optical axis of the optical unit and the orientation of the lens (tilting) influences glare/reflections. Particularly, the respective current first and second parameters are stored together with the corresponding current spatial position and orientation of the lens for later comparison.

Preferably, depending on the first and second parameter, a new spatial position and/or orientation of the additional lens is automatically determined, and the additional lens is automatically moved into said new spatial position and/or orientation in order to maximize the first and second parameter, wherein particularly depending on the first parameter also a new incidence angle may be automatically determined and the lighting unit will be automatically rotated (about a vertical axis) so as to let the light beam have said new incidence angle in order to maximize the first parameter also with respect to said incidence angle.

The new spatial lens position, orientation and particularly incidence angle leads again to a new current image of the observed eye structure, for which the first and second parameter are automatically determined again, in order to iteratively determine an optimal spatial position and orientation of the additional lens and particularly also incidence angle, thus maximizing said first and second parameter.

Preferably, the first and/or second parameter is optimized with respect to the spatial position and orientation of the additional lens (eventually also with respect to said incidence angle) by means of a Simplex algorithm.

The analyzing unit may be formed by a computer being connected to the at least one camera and the controlling units of the actuator means, wherein a suitable program (stored in the computer's memory) may be designed to perform the above described maximization (optimization).

Particularly, the system (device) and method according to the invention works independently from adjustments of the lighting unit (slit lamp) or the gaze position of the patient's eye. In case one of these changes, the optimization procedure will start over again.

Further features and advantages of the invention shall be described by means of detailed descriptions of embodiments with reference to the Figures, wherein FIG. 1 shows a schematic overview of the setup for a fundus investigation using a stereomicroscope and a slit lamp as lighting unit;

The device 1 and method according to the invention may be used during regular fundus observation using a lighting unit 60 in the form of a slit lamp.

Figure 1:
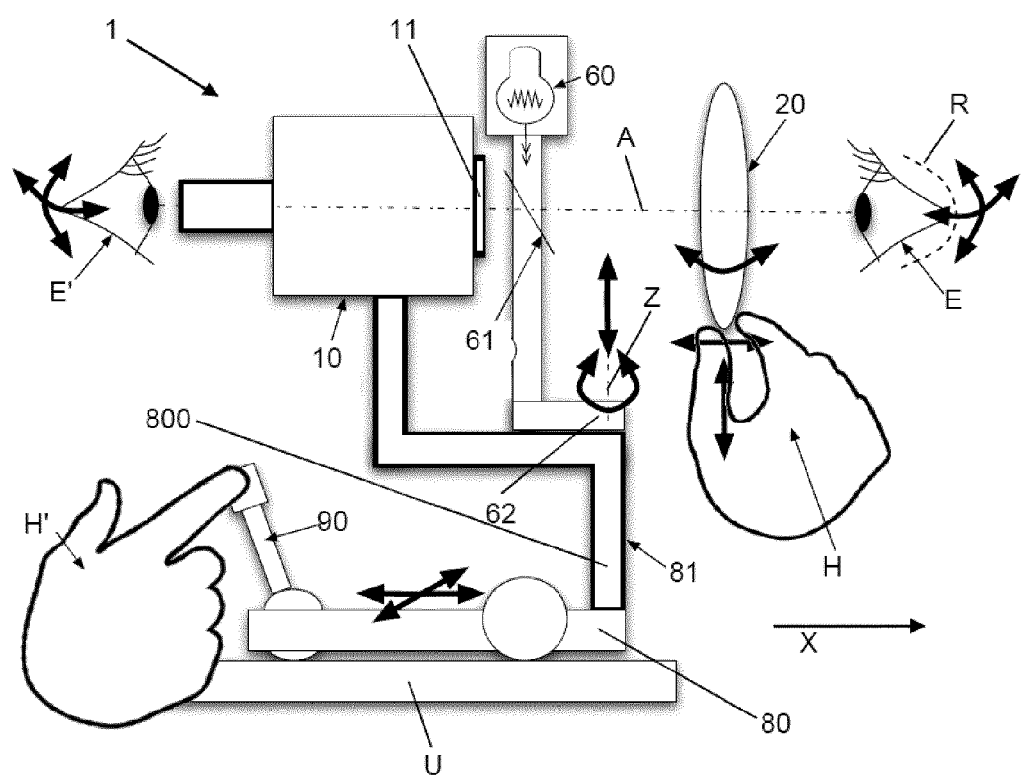

As shown in FIG. 1 regular devices using stereomicroscopes for fundus observation consist of an optical unit (main body) 10 containing the optics and some mechanical supports 80. Because of a revolving joint 81 the main body 10 can be rotated around a vertical axis Z. The main body 10 can also be translated on a table U in two directions using a joystick 90. Finally, another revolving joint 62 integrated into a main holder 800 allows for raising or lowering the main body 10 by rotating the joystick 90. Using one hand H' the ophthalmologist adjusts with the aforementioned revolving joints 62, 81 the position and orientation of the device 1 relatively to the patient's eye E in order to see the fundus (retina) R of the patient's eye E. During the investigation he has to position his eyes E' in front of an ocular 12 of the optical unit (main body) 10. With the other hand H, he has to hold the additional lens 20 into the optical path A between the main body 10 and the patient's eye E. The light coming from the illumination system (lighting unit) 60 will be coupled into the optical path A by using a mirror 61 of the lighting unit 60 (e.g. a slit lamp).

The ophthalmologist can change the incidence of light by rotating the lighting unit 60 about the same vertical axis Z as the main body 10. The light coupled into the system causes reflections and glare on the surface of the additional lens 20.

During the investigation the ophthalmologist has to optimize the position of the lighting unit (slit lamp) 60, i.e. the incidence angle of the light beam generated by the lighting unit 60, the position of his eyes E' and the position of the additional lens 20, in order to get a sharp and glare free image of the retina R. Moreover, he has to continuously realign all components if the patient is moving or if he wants to examine another part of the retina R.

Figure 2:
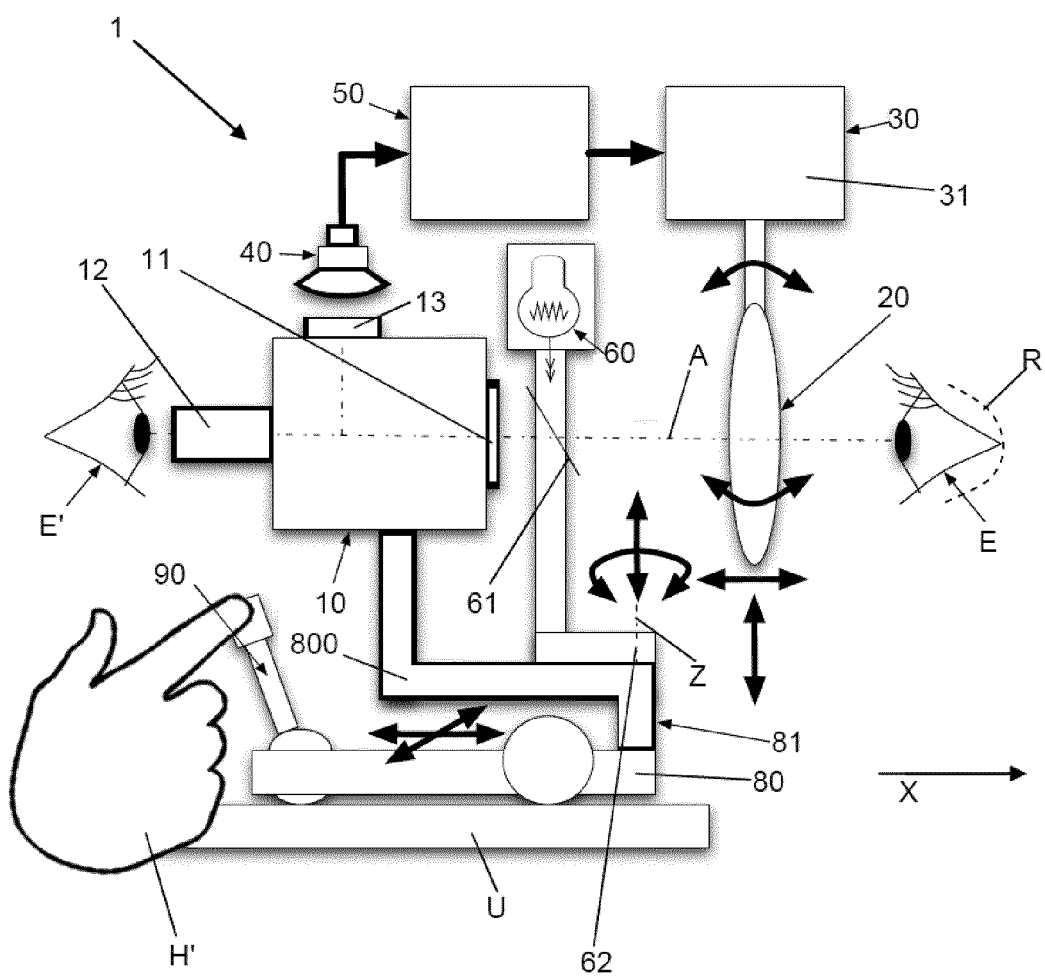
FIG. 2 shows a device according to the invention equipped with a CCD camera deriving the live image as seen by the ophthalmologist, wherein a first actuator means manipulates only the spatial position and orientation of the additional lens.
Figure 3:
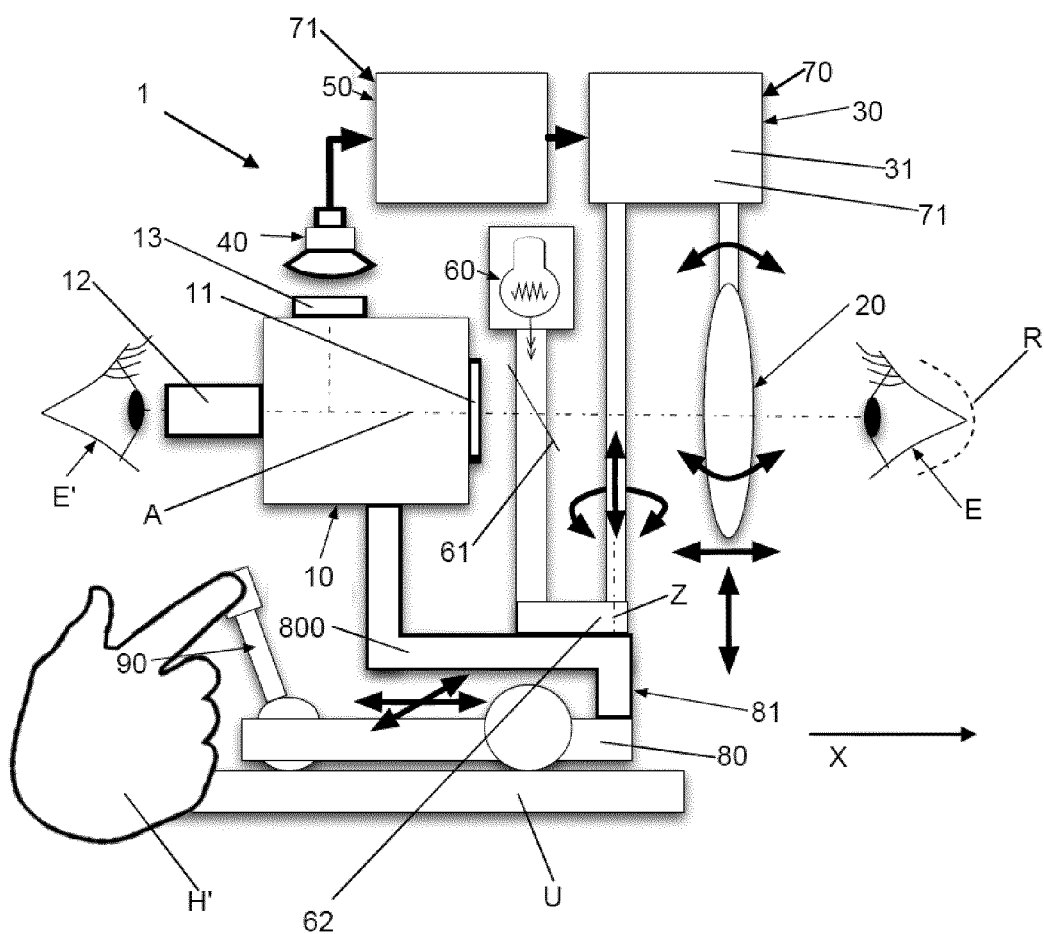
FIG. 3 shows a device according to the invention equipped with a CCD camera deriving the live image as seen by the ophthalmologist, wherein the actuator means actively manipulate the spatial position and orientation of the additional lens as well as the incidence angle of the light beam of the lighting unit (slit lamp)

Different embodiments of a device 1 according to the present invention are shown in FIGS. 2 and 3. In both embodiments the additional lens 20 is carried by a first actuator means 30 aligning automatically the spatial position (position of the center of mass or another reference point of the additional lens 20) and orientation of the additional lens 20 (i.e. the additional lens 20 can be tilted with respect to the optical axis A) in order to optimize the image I seen by the ophthalmologist.

As shown in FIGS. 2 and 3 the main body (optical unit) 10 is connected to a carrier 80 that is designed to rest on a table U or another bottom, wherein the carrier 80 can be translated along the surface of the table U along a horizontal direction X by means of a third actuator means.

The optical unit 10 comprising a stereomicroscope having an objective 11 and an ocular 12 as well as at least one CCD camera 40 coupled to the optical path/axis A by means of a suitable means (e.g. adaptor or interface) 13 is connected to said carrier 80 through a main arm 800 which is connected via a revolving joint 81 to said carrier 80 so that the optical unit 10 can be rotated about a vertical axis Z by means of a fourth actuator means (not shown).

The optical unit 10 is further mounted to the carrier 80 such that it can be moved along a vertical direction Z with respect to the carrier 80 by means of a fifth actuator means (not shown). The optical unit 10 may be displaced vertically along the main arm 800.

The device 1 further comprises a lighting unit 60 in the form of a slit lamp that generates a slit-like light beam reflected along the optical axis A of the optical unit 10 by means of a mirror 61 in order to illuminate the fundus R of the patient's eye E.

Thus, an intermediate image of the posterior structure (retina) R of the patient's eye is generated by means of the additional lens 20 positioned in front of the patient's eye E along the optical path/axis A, which intermediate image can be viewed by means of the optical unit 10 (e.g. stereomicroscope) that creates the current image I of the posterior structure R from said intermediate image.

The lighting unit 60 is also connected to the carrier 80, particularly to said main arm 800 via a revolving joint 62 such that it can be rotated about the same vertical axis Z like the optical unit 10, for instance by means of a second actuator means 70 (cf. FIG. 3).

The above described adjustments may be actuated by means of a joystick 90 arranged on the carrier 80.

Figure 5:
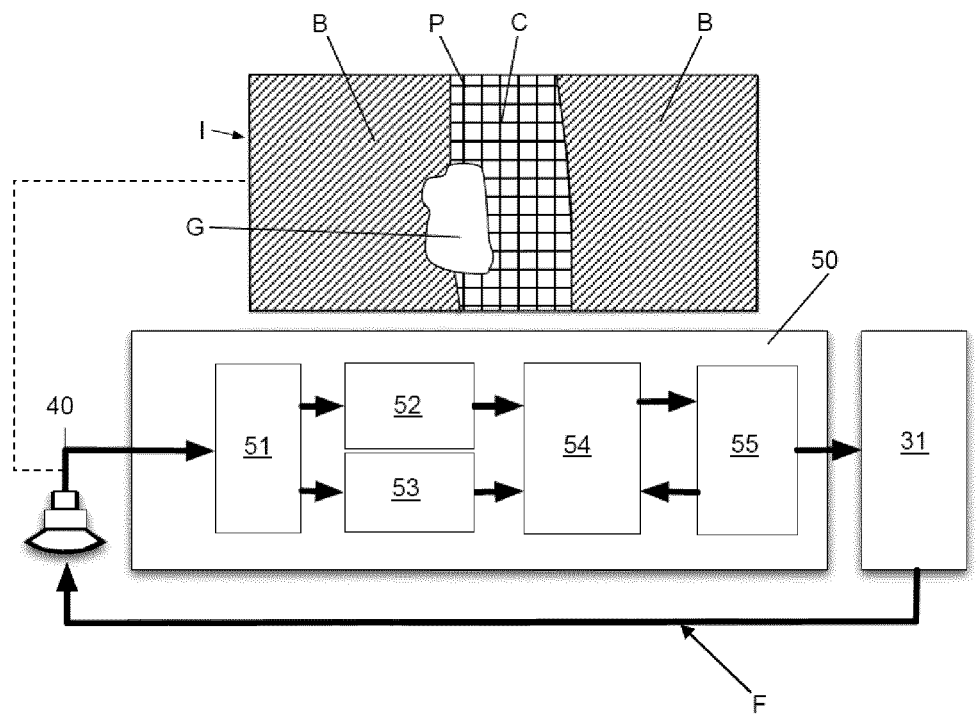
FIG. 5 shows a schematical representation of the signal processing chain of the device and method according to the invention.

To assess the visual information that the ophthalmologists sees (i.e. current image I as shown in FIG. 5) the stereomicroscope of the optical unit 10 is equipped with one or two (video) cameras 40 (CCD) deriving one or both view channels from the stereomicroscope. The derived video signals are processed and analyzed using an analyzing unit 50 that may be formed by a computer executing a corresponding software. The processing aims first at identifying the content of interest in the live video stream, i.e., the current image I. The analyzing (processing) unit 50 has to separate automatically the parts of the current image I showing retina R (region C) from the parts of the current image I belonging to the background B and the parts of the current image I containing glare or reflections (reflection region(s) G), cf. FIG. 5. After classification of said image parts the system 1 has to determine the size of the retina part C and the size of the glare/reflections part G. Additionally, the system 1 has to determine the image sharpness of the part C showing retina in the image I. Based on these values (ratio between areas C showing retina and containing glare/reflections G and the sharpness in the retina sub-image C) the processing unit 50 generates signals for a first controlling unit 31 of the first actuator means 30 that will lead to a corresponding new spatial position and orientation of the additional lens 20. The device 1 consisting of the (video) camera(s) 40, the analyzing (processing) unit 50, the first actuator means 30, and the additional lens 20 works like a closed-loop control optimizing the spatial position and the orientation of the additional lens 20 in order to maximize the shown retina content C while minimizing the glare and the reflection G and maximizing the sharpness in the retina sub-image part C, cf. FIG. 5.

Generally, the optimization procedure may run continuously during the examination or it can be triggered manually by pushing a button on the joystick 90.

In the embodiment shown in FIG. 2, the spatial position and the orientation of the lens 20 is actively controlled by said closed loop system. The illumination system (lighting unit) 60 remains independent from this closed loop system. The ophthalmologist is free to change the incidence angle of the illumination. Additionally, he can translate the optical unit (main body) 10 by tilting the joystick 90 and raising/lowering the main body 10 by turning the joystick 90, see above.

In the embodiment shown in FIG. 3 the incidence angle of the illumination system 60 is controlled by the closed loop system, too. Thus, the system 1 optimizes both the spatial position and the orientation of the additional lens 20 as well as said incidence angle in order to minimize the reflections G. The ophthalmologist thus is free to translate the main body 10 by tilting the joystick 90 and raising/lowering the main body 10 by turning the joystick 90.

Figure 4:
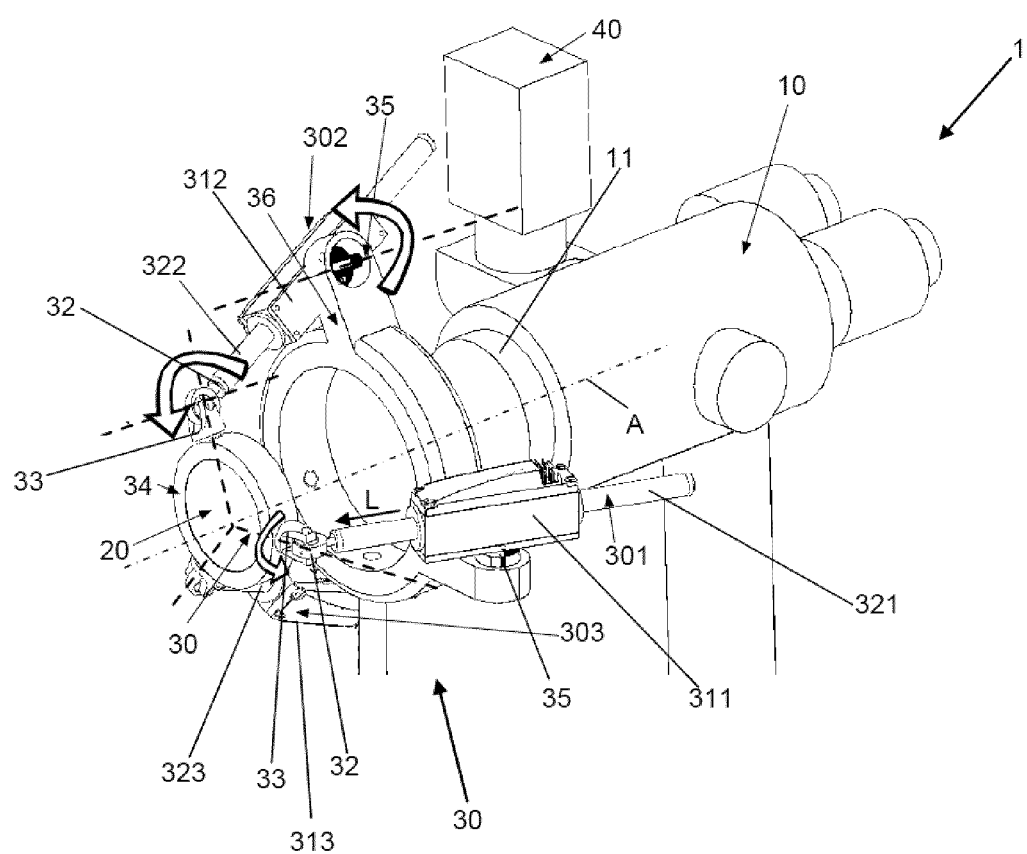
FIG. 4 shows a device according to the invention having a tip-tilt-piston kinematics to alter the spatial position and orientation of the additional lens.

To alter the spatial position and the orientation of the additional lens 20 with high dynamics ideally a parallel kinematics is used. A corresponding embodiment utilizes a so-called "tip-tilt-piston" kinematics as illustrated in FIG. 4. The additional lens 20 is mounted in a first retainer 34 (also denoted as top platform) circulating the additional lens 20, which first retainer 34 is coupled to a circulating second retainer 36 (also denoted as base platform), which is rigidly connected to the optical unit (main body) 10. Both retainers 34, 36 thus form a through opening through which the optical path/axis A extends. The first retainer 34 is connected to the second retainer (#13) via three linear actuators 301, 302, 303. On the second retainer side these linear actuators 301, 302, 303 are each connected with a first element 311, 312, 313 via a revolving joint 35 to the second retainer 36. The first retainer 34 connects to a second element 321, 322, 323 of each linear actuator 301, 302, 303 by means of two revolving joints 32, 33, which second element 321, 322, 323 is guided by the respective first element 311, 312, 313 and can be displaced along its respective extension direction L with respect to the respective first element 311, 312, 313.

The degrees of freedom thus introduced by the three joints for each linear actuator 301, 302, 303 allow for tilting the additional lens 20 in two directions (adjustment of the orientation of the additional lens 20) and for moving the first retainer 34, i.e., the additional lens 20, along the optical path/axis A. Beyond that the construction is rigid.

Other embodiments might utilize more complex parallel kinematics such as a hexapod kinematics. However, a serial kinematics is also conceivable in other embodiments.

In general, moving the additional lens 20 along the optical axis A changes the sharpness of the current image I as seen by the ophthalmologist. Tilting the additional lens 20 reduces the glare and reflections G.

Finally, FIG. 5 describes a possible signal processing chain of the device 1 or method according to the invention in a specific embodiment. The current (live) image I coming from the camera 40 is schematically shown in FIG. 5 in the upper part. Most of the slit lamp image I contains usually background B. The central part might contain retina information (region C) and can be cluttered by spots of glare and reflections e.g. the area/region denoted as G. The signal processing unit (analyzing unit) 50 analyses the current (video) image I stepwise. In a first step a classifier 51 is used to segment the current image I. In a specific embodiment of this invention a Bayesian network also known as belief network can be used to implement a classifier 51. Based on a training set of slit lamp images the probability that a pixel P in the image I belongs to either background B, content C, or reflection G can be determined using pixel properties such as pixel color information, entropy in the local pixel environment, or pixel position. Each pixel P in the image is classified using such mechanism. In a next step 52 the sharpness in the area of the sub-image C (the area that contains retina R) is assessed. In a specific embodiment a gradient-based approach is used. This means the sub-image C is filtered using a Holoborodko kernel (or any other suitable kernel) then a histogram will be computed and the histogram distribution will be evaluated. If the pixel distribution within the histogram is rather equal the sub image C is blurry. The more significant the peaks are in the histogram of the sub-image C, the sharper the current image I is. The sub component 53 computes the ratio between the size of the retina content C and the glare/reflection region G. Both, the ratio between the area sizes as well as the sharpness of the retina sub image C have to be maximized. The current values for the sub-image size-ratio and sharpness of the retina sub-image C are stored together with the current spatial position and the current orientation of the additional lens 20 for later comparison 54. Both values are optimized separately because the sharpness depends on the spatial lens position along the optical axis A of the system 1 and the lens tilting (orientation) influences glare/reflections. In a specific embodiment a Simplex optimizer 55 is used. Based on the optimization results a new spatial position and a new orientation of the additional lens 20 will be send to the actuator control unit 31 (and eventually 71, see above). The new spatial lens position/lens orientation leads again to a new current (video) image, which will be evaluated in a next step in order to move the additional lens 20 into its optimal lens position and orientation (and eventually to find an optimal incidence angle, too). Thus a feedback loop F is established.

The invention claimed is:

1. Device for examining an eye, comprising:
   an optical unit that is designed to generate a current image of a current intermediate image, wherein the optical unit comprises an objective,
   an additional lens that is designed to be arranged between said objective and an eye along an optical axis of the optical unit in order to generate said current intermediate image,
   wherein said additional lens is designed to be movable relative to said optical unit, particularly so as to generate a sharp and reflection-free current image of said posterior structure with help of said optical unit and said additional lens, and
   wherein the device comprises a first actuator means that is designed to move the additional lens,
   wherein
   the device is designed to control said first actuator means depending on the current image.

2. Device as claimed in claim 1, wherein the optical unit comprises at least one camera for capturing said current image.

3. Device as claimed in claim 2, wherein said at least one camera is formed by a CCD camera.

4. Device as claimed in claim 1, wherein the device comprises a first controlling unit being designed to control the first actuator means.

5. Device as claimed in claim 4, wherein the first controlling unit is designed to control the first actuator means for moving the additional lens into the respective new position of the additional lens determined by the analyzing unit.

6. Device as claimed in claim 1, wherein the device comprises an analyzing unit being designed to analyze the current image in order to determine at least one parameter associated to the current image.

7. Device as claimed in claim 6, wherein the analyzing unit is designed to determine, depending on the first parameter, also a new incidence angle of the light beam in order to maximize the first parameter with respect to the position of the additional lens and the incidence angle of the light beam.

8. Device as claimed in claim 6, wherein the ratio between the size of a region of the current image containing posterior structure information and the size of a reflection region of said current image is determined as a first parameter.

9. Device as claimed in in claim 8, wherein the sharpness of said region of the current image containing posterior structure information is determined as a second parameter.

10. Device as claimed in in claim 8, wherein the analyzing unit is designed to determine a new position into which the additional lens is to be moved in order to maximize said at least one parameter with respect to the position of the additional lens.

11. Device as claimed in claim 1, wherein the first actuator means is designed to adjust the spatial position and/or orientation of the additional lens with respect to the optical unit.

12. Device as claimed in claim 11, wherein the first actuator means comprises a first, a second and a third linear actuator, wherein each of the linear actuators comprises a first element and a second element, wherein each second element can be moved with respect to the associated first element along an extension direction of the respective second element, wherein the second elements are each connected with a free end via two revolving joints to a first retainer retaining the additional lens, and wherein the first elements are each connected via a revolving joint to a second retainer being rigidly connected to the optical unit, and wherein the second retainer opposes the first retainer along the optical axis.

13. Device as claimed in claim 1, wherein the device comprises a lighting unit.

14. Device as claimed in claim 13, wherein the lighting unit can be rotated about a vertical axis in order to adjust an incidence angle with which said light beam impinges on the additional lens.

15. Device as claimed in claim 13, wherein the device comprises a second actuator means for rotating the lighting unit about the vertical axis.

16. Device as claimed in claim 15, wherein the device comprises a second controlling unit being designed to control the second actuator means.

17. Device as claimed in claim 16, wherein the second controlling unit is designed to control the second actuator means for rotating the lighting unit so that the light beam impinges on the additional lens with the new incidence angle determined by the analyzing unit.

18. Device as claimed in claim 15, wherein the device comprises an actuating means for actuating the second, third, fourth and/or fifth actuator means.

19. Device as claimed in claim 18, wherein said actuating means is formed as a joystick.

20. Device as claimed in claim 13, wherein the lighting unit is connected to the carrier via a revolving joint such that it can be rotated about a vertical axis.

21. Device as claimed in claim 13, wherein the lighting unit is in the form of a slit lamp that is designed to generate a light beam along the optical axis of the optical unit in order to illuminate the posterior structure to be examined.

22. Device as claimed in claim 13, wherein the lighting unit comprises a mirror for reflecting the light beam along the optical axis.

23. Device as claimed in claim 1, wherein the optical unit comprises a stereomicroscope having said objective.

24. Device as claimed in claim 1, wherein the device comprises a carrier for supporting the optical unit, which carrier is designed to be movable along a horizontal direction.

25. Device as claimed in claim 24, wherein the optical unit is connected to said carrier via a revolving joint so that the optical unit can be rotated about a vertical axis.

26. Device as claimed in claim 25, wherein the device comprises a fourth actuator means that is designed to rotate the optical unit about said vertical axis.

27. Device as claimed in claim 24, wherein the optical unit is connected to the carrier such that it can be moved along a vertical direction with respect to the carrier.

28. Device as claimed in claim 27, wherein the device comprises a fifth actuator means that is designed to move the optical unit along said vertical direction.

29. Device as claimed in claim 24, wherein the device comprises a third actuator means that is designed to move the carrier along said horizontal direction.

30. Device as claimed in claim 1 for examining a human eye.

31. Device as claimed in claim 1, wherein said current intermediate image is of a posterior structure of said eye.

32. Method for examining an eye comprising the steps of:
    arranging an additional lens between an eye and an objective of an optical unit so as to generate a current image of a posterior structure of said eye by means of said optical unit and said additional lens, and
    moving said additional lens automatically with respect to said objective depending on the current image in order to reduce reflections and/or increase the sharpness of the current image of the posterior structure.

33. Method according to claim 32, wherein the current image is captured by at least one camera.

34. Method as claimed in claim 33, wherein in order to determine said first parameter, each pixel of the current image is automatically classified to belong to either background containing no posterior structure information, said region containing posterior structure information, or said reflection region.

35. Method as claimed in claim 34, wherein said classification is preferably performed using a Bayesian classifier.

36. Method as claimed in claim 33, wherein in order to determine said second parameter, said region containing posterior structure information is partially differentiated, particularly using a gradient operator.

37. Method as claimed in claim 36, wherein in order to determine said second parameter, said region containing posterior structure information is partially differentiated using a gradient operator.

38. Method as claimed in claim 37, wherein the gradient operator is a Holoborodko Kernel, and the pixel distribution of said derivative is computed.

39. Method according to claim 33, wherein the at least one camera, is a CCD camera.

40. Method according to claim 33, wherein the current image is represented by a plurality of pixels.

41. Method as claimed in claim 32, wherein at least one parameter associated to the current image is automatically determined.

42. Method as claimed in claim 41, wherein the first and/or second parameter is automatically maximized with respect to the position of the additional lens.

43. Method as claimed claim 42, wherein the first and/or second parameter is automatically maximized with respect to the position of the additional lens with respect to the spatial position of the additional lens as well as with respect to the orientation of the additional lens.

44. Method as claimed claim 43, wherein the first parameter is also maximized with respect to an incidence angle of a light beam generated by a lighting unit for illuminating the posterior structure to be examined, with which incidence angle said light beam impinges on the additional lens.

45. Method as claimed in claim 41, wherein the first and the second parameter are maximized separately.

46. Method as claimed in claim 45, wherein the respective current first and second parameters are stored together with the corresponding current spatial position and orientation of the additional lens.

47. Method as claimed in claim 41, wherein depending on the first and second parameter a new position of the additional lens is automatically determined, and the additional lens is automatically moved into said new position in order to maximize the first and second parameter.

48. Method according to claim 47, wherein the new position of the additional lens leads again to a new current image, for which the first and second parameter are automatically determined again, in order to iteratively determine an optimal position of the additional lens.

49. Method according to claim 48, wherein the new incidence angle leads again to a new current image, for which the first and second parameter are automatically determined again, in order to iteratively determine an optimal position of the additional lens.

50. Method according to claim 49, wherein also an optimal incidence angle maximizing said first and second parameter.

51. Method as claimed in claim 47, wherein depending on the first and second parameter a new spatial position and orientation, of the additional lens is automatically determined, and the additional lens is automatically moved into said new position in order to maximize the first and second parameter.

52. Method as claimed in claim 51, wherein depending on the first parameter also a new incidence angle is determined and the lighting unit is automatically rotated so as to let the light beam have said new incidence angle in order to maximize the first parameter.

53. Method as claimed in claim 41, wherein the first and/or second parameter is maximized using a Simplex algorithm.

54. Method as claimed in claim 41, wherein the ratio between the size of a region of the current image containing posterior structure information and the size of a reflection region of said current image is determined as a first parameter.

55. Method as claimed in claim 54, wherein the sharpness of said region of the current image containing posterior structure information is determined as a second parameter.

56. Method as claimed in claim 32 for examining a human eye.

57. Method as claimed in claim 32 using a device according to claim 1.

* * * * *

UNITED STATES PATENT AND TRADEMARK OFFICE
CERTIFICATE OF CORRECTION

PATENT NO.        : 9,277,861 B2                           Page 1 of 1
APPLICATION NO.   : 14/365234
DATED             : March 8, 2016
INVENTOR(S)       : Jens Kowal et al.

It is certified that error appears in the above-identified patent and that said Letters Patent is hereby corrected as shown below:

ON THE TITLE PAGE:

At item (73), Assignee, change "UNIVERSITÄT BERN, Bern (SE)" to --UNIVERSITÄT BERN, Bern (CH)--.

Signed and Sealed this
Twenty-fourth Day of May, 2016

Michelle K. Lee
*Director of the United States Patent and Trademark Office*